United States Patent [19]

Stevens

[11] 4,022,216
[45] May 10, 1977

[54] UROLOGICAL CATHETER

[76] Inventor: Robert C. Stevens, 2451 Brickell Ave., Miami, Fla. 33129

[22] Filed: Aug. 11, 1975

[21] Appl. No.: 603,699

[52] U.S. Cl. .......................................... 128/349 B
[51] Int. Cl.² ........................................ A61M 25/00
[58] Field of Search ..... 128/349 B, 349 R, 349 BV, 128/351

[56] References Cited

UNITED STATES PATENTS

| | | | |
|---|---|---|---|
| 550,238 | 11/1895 | Allen, Jr. | 128/349 B |
| 1,763,079 | 6/1930 | Zacsek | 128/349 B |
| 1,922,084 | 8/1933 | Gerow | 128/349 B |
| 3,045,677 | 7/1962 | Wallace | 128/349B |
| 3,053,257 | 9/1962 | Birtwell | 128/349 B |
| 3,926,705 | 12/1975 | Todd | 128/349 B |

Primary Examiner—Stephen C. Pellegrino
Attorney, Agent, or Firm—Kenway & Jenney

[57] ABSTRACT

Disclosed is a urological catheter equipped, at its distal portion, with a pair of balloons inflatable from the proximal end of the catheter. One balloon completely covers the distal tip of the catheter to serve, when inflated, as a cushion preventing damage to the patient's bladder, while the other balloon serves to anchor the catheter in sealing relation to the discharge passage of the bladder. A drainage opening in the catheter wall is disposed intermediate the balloons.

1 Claim, 4 Drawing Figures

U.S. Patent   May 10, 1977   4,022,216
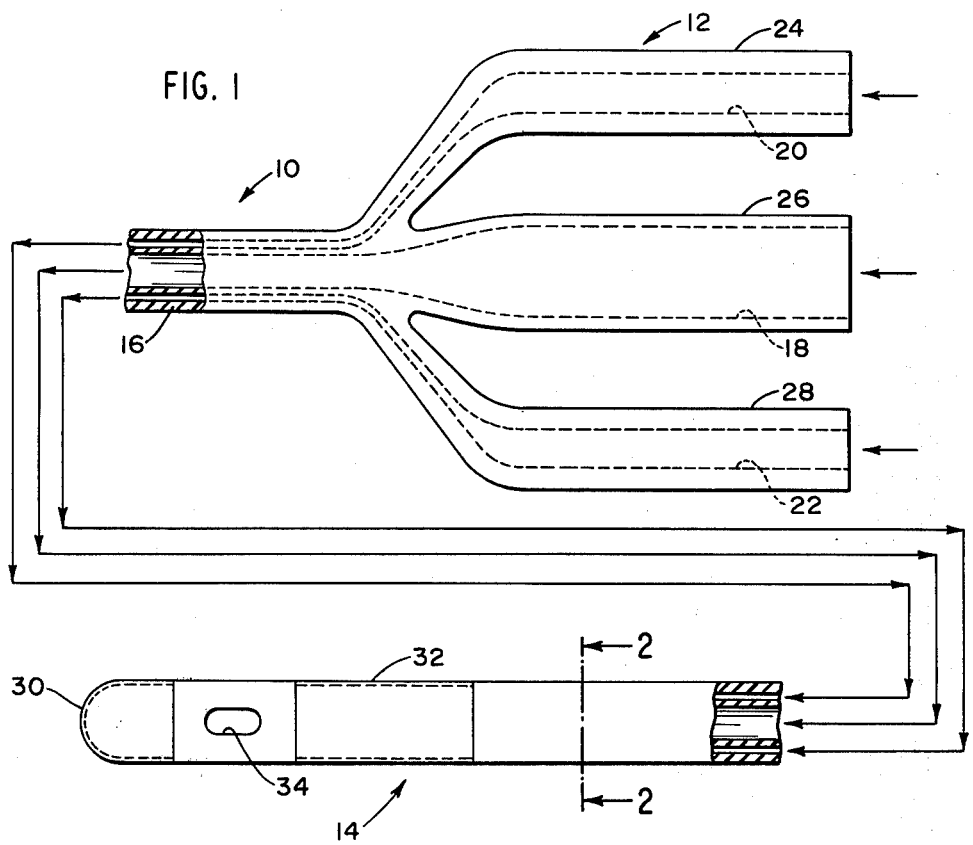
FIG. 1
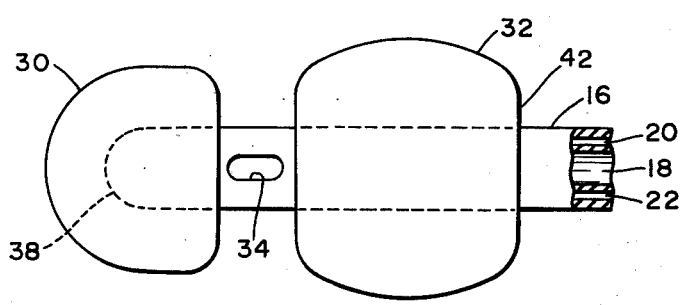
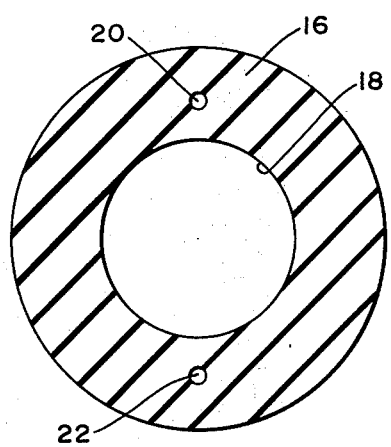
FIG. 2
FIG. 3
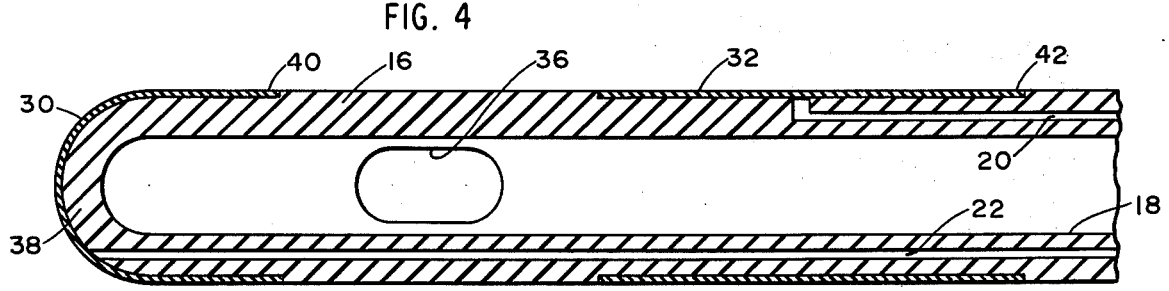
FIG. 4

UROLOGICAL CATHETER

BACKGROUND OF THE INVENTION

The present invention relates to urological catheters and, in particular, to improvements in such catheters which render them less likely to injure the delicate bladder tissue and/or to cause discomfort to the patient.

Urological catheters employing retention balloons, inflatable after insertion into the patient's bladder, have been known for some time. Such catheters, however, have often caused injury and/or discomfort to the patient in at least two different ways. First, since the catheter must be made sufficiently rigid to permit insertion into the bladder and to prevent collapse of the catheter wall and blockage of the drainage lumen, the distal tip of the catheter is typically sufficiently rigid to irritate, and even cause damage to, the bladder wall. Second, the bladder can collapse over the drainage eye thereby blocking the drainage path for fluid from the bladder and potentially damaging bladder tissue if a column of liquid in the drainage lumen produces a high level of suction at the drainage eye.

In view of the foregoing, among the objects of the present invention may be noted the provision of a urological catheter which both prevents damage to the bladder wall and prevents occlusion of the catheter's drainage opening by the bladder tissue itself. Other objects, features, and advantages of the invention will be partly apparent and partly pointed out in the description below.

SUMMARY OF THE INVENTION

Briefly, the invention features a urological catheter having a distal portion for insertion into a patient's bladder and a pair of longitudinally spaced inflatable balloons secured to that distal portion. A first balloon envelops the closed distal tip of the catheter, thereby, when inflated, cushioning that tip and preventing contact of the bladder tissue by the tip. The second balloon is a retention balloon and is spaced apart from the first balloon with the drainage eye disposed intermediate the two balloons, whereby the inflated balloons serve to inhibit the occlusion of the drainage eye should the bladder wall collapse against the catheter.

BRIEF DESCRIPTION OF THE DRAWING

FIG. 1 is a partially broken-away, partially schematic illustration of a urological catheter constructed in accordance with the present invention;

FIG. 2 is a sectional view taken at 2—2 of FIG. 1;

FIG. 3 is a view of the distal end portion of the catheter of FIG. 1 with its balloons inflated; and FIG. 4 is a vertical section of the distal end portion of the catheter of FIG. 1.

DETAILED DESCRIPTION OF A PARTICULAR PREFERRED EMBODIMENT

Referring to the drawing, the catheter 10 includes a proximal end portion 12 and a distal end portion 14. The catheter 10 is formed as a hollow tube made from a material that is inert and is flexible and resilient enough for insertion through tortuous body passages, while being rigid enough to prevent a collapse of the catheter walls with consequent blockage of one or more catheter passages. A presently preferred material is polytetrafluoroethylene-coated latex. But for the proximal end portion 12, the catheter is formed as a hollow annular tube 16 with an outer diameter of 0.25 inch and a central drainage lumen or passage 18 having a diameter of 0.13 inch. Axially extending inflation lumens or passages 20 and 22 are provided in the wall of tube 16. At the proximal end portion 12, the tube 16 forks to provide three separate tubes 24, 26, and 28 defining, respectively, the three passages 20, 18, and 22. This structure at the proximal end portion facilitates the connection of inflation devices to the passages 20 and 22 and a drainage tube, or other implement, to the passage 18.

The distal end portion 14 is provided with a pair of inflatable balloons 30 and 32 and a pair of drainage eyes 34 and 36 intermediate the balloons. As best seen in FIG. 4, the first balloon 30 envelops the closed tip 38 of the distal end portion 14 and is attached to the distal end portion by any conventional means along a single line of attachment 40 which extends around the full circumference of the tube 16. The inflation lumen 22 communicates with the interior of the balloon 30. The second balloon 32 is secured around the circumference of the tube 16 at a location spaced apart from the tip 38 and the inflation passage 20 communicates with the interior of balloon 32. The drainage eyes 34, 36 are generally rectangular in shape, but with rounded corners, and are approximately 0.20 by 0.10 inch. In the preferred embodiment illustrated, the drainage eyes 34, 36 are spaced apart from each of the balloons 30 and 32 by distance of about 0.10 inch. Again referring to FIG. 4, in the deflated condition, balloon 20 has an axial length of about 0.30 inch and the balloon 32 has an axial length of about 0.60 inch. The total length of the distal end portion 14 from the tip 38 to the proximal end 42 of balloon 32 is about 1.3 inches, thus, facilitating insertion of the entire distal end portion 14 into the bladder of a patient.

In the operation of the catheter, the distal end portion 14 is inserted into the patient's bladder and then, using conventional inflation means coupled to tubes 24 and 28 at the proximal end portion 12, the balloons 30 and 32 are inflated. When inflated to conventional pressures, the balloon 30 has a volume of approximately 4cc and the balloon 32 has a volume of 5cc. The balloon 32 will be disposed adjacent to the mouth of the urethera, thus helping retain the catheter in position in the bladder and also sealing the mouth of the urethera. The balloon 30 envelops the semi-rigid tip 38 of the distal end portion thereby cushioning it against damaging or uncomfortable contact with the bladder wall. Furthermore, the provision of the baloons 30 and 32 closely adjacent, but spaced from the drainage eyes 34 and 36 prevents the bladder wall from collapsing against those drainage eyes and occluding them, with attendant interruption of drainage and possible damage to the bladder tissue.

It will thus be appreciated that the present invention achieves the objects and advantages set out above. Furthermore, while a particular preferred embodiment has been illustrated in the accompanying drawing and described in detail herein, other embodiments are within the scope of the invention and the following claims.

I claim:

1. In a urological catheter comprising an elongated tubular member having a proximal end portion, a distal end portion for insertion into the bladder of a patient, a fluid passage extending from said proximal end portion to a draining eye in said distal end portion inflatable balloon means on said distal end portion and passage means leading from said proximal end portion to the interior of said balloon means, the improvement wherein said distal end portion has a closed tip, a first inflatable balloon enveloping said tip to prevent contact of bladder tissue by said tip, and attached to said member in a single zone of attachment that extends around the entire circumference of said member, and a second inflatable balloon attached to said member at a location spaced apart from said first balloon;

said drainage eye disposed intermediate said first and second balloons, thereby enabling said balloons to restrain collapsed bladder tissue from occluding said said drainage eye;

the distance along said distal end portion from said tip to the portion of said second balloon most remote from said tip is between about 1 and 2 inches;

the distance between said drainage eye and each of said balloons is about 0.1 inch.

* * * * *